US010519521B2

(12) United States Patent
Wen et al.

(10) Patent No.: US 10,519,521 B2
(45) Date of Patent: Dec. 31, 2019

(54) METHOD OF PREVENTING CARBOHYDRATE CRYSTALLIZATION

(71) Applicant: The Trustees of California State University, Los Angeles, CA (US)

(72) Inventors: Xin Wen, Alhambra, CA (US); Sen Wang, Alhambra, CA (US)

(73) Assignee: The Trustees of California State University, Los Angeles, CA (US)

( * ) Notice: Subject to any disclaimer, the term of this patent is extended or adjusted under 35 U.S.C. 154(b) by 291 days.

(21) Appl. No.: 15/067,012

(22) Filed: Mar. 10, 2016

(65) Prior Publication Data

US 2016/0265073 A1  Sep. 15, 2016

Related U.S. Application Data

(60) Provisional application No. 62/132,398, filed on Mar. 12, 2015.

(51) Int. Cl.
| | | |
|---|---|---|
| C13K 13/00 | (2006.01) | |
| C07K 14/43 | (2006.01) | |
| C07K 14/435 | (2006.01) | |

(52) U.S. Cl.
CPC ........ *C13K 13/00* (2013.01); *C07K 14/43563* (2013.01)

(58) Field of Classification Search
CPC ............................ C13K 13/00; C07K 14/43563
See application file for complete search history.

(56) References Cited

U.S. PATENT DOCUMENTS

| | | | | | |
|---|---|---|---|---|---|
| 5,358,931 | A | * | 10/1994 | Rubinsky | A01N 1/02 424/523 |
| 5,605,837 | A | * | 2/1997 | Karimi | G01N 33/96 252/408.1 |
| 5,627,051 | A | * | 5/1997 | Duman | C07K 14/43563 435/69.1 |
| 5,633,451 | A | * | 5/1997 | Duman | C07K 14/43563 435/419 |
| 9,394,327 | B1 | * | 7/2016 | Wen | C07H 1/06 |
| 2013/0153818 | A1 | * | 6/2013 | Oyaizu | A23L 3/37 252/70 |
| 2015/0079254 | A1 | * | 3/2015 | Ramlov | A01N 1/02 426/327 |

OTHER PUBLICATIONS

Andorfer et al., 2000, Isolation and characterization of cDNA clones encoding antifreeze proteins of the pyrochroid beetle Dendroides Canadensis, Journal of Insect Physiology, 46: 365-372.*
Amornwittawat et al., 2009, Effects of polyhydroxy compounds on beetle antifreeze protein actitivty, Biochim Biophys Acta, 1794(2): 341-346.*
Amornwittawat et al., 2008, Polycarboxylates Enhance Beetle Antifreeze Protein Activity, Biochim. Biophys. Acta., 1784(12): 1942-1948.*
Amornwittawat, N. et al. (2009). Effects of polyhydroxy compounds on beetle antifreeze protein activity. Biochimica et Biophysica Acta 1794,341-346.
Duman, J. G, et al. (1998), Molecular characterization and sequencing of antifreeze proteins from larvae of the beetle *Dendroides canadensis*. J Comp Physiol B. 168: 225-232.
Elbein, A, et al. (2003). New insights on trehalose: a multifunctional molecule. Glycobiology 13(4), 17R-27R.
Sarkar, S, et al. (2007), Trehalose, a Novel mTOR-independent Autophagy Enhancer: Accelerates the Clearance of Mutant Huntingtin and alpha-Synuclein. J Bio Chem, 282(8), 5641-5652.
Nishizaki, Y, et al. (2000). Disaccharide-Trehalose Inhibits Bone Resorption in Ovariectomized Mice. Nutrition Research, 20(5), 653-664.
Kandror, O, et al. (2002). Trehalose synthesis is induced upon exposure of *Escherichia coli* to cold and is essential for viability at low temperatures. PNAS 99(15), 9727-9732.
Gibney, P, et al. (2015). Characterizing the in vivo role of trehalose in *Saccharomyces cerevisiae* using the AGT1 transporter. PNAS 112(19), 6116-6121.
Sundaramurthi, P. and Suryanarayanan, R. (2010), Trehalose Crystallization During Freeze-Drying: Implications On Lyoprotection. J. Phys. Chem. Lett. 1, 510-514.
Wang, S. et al. (2009). Arginine, a Key Residue for the Enhancing Ability of an Antifreeze Protein of the Beetle *Dendroides canadensis*. Biochemistry. 48, 9696-9703.
Wang, S, et al. (2012), Expanding the molecular recognition repertoire of antifreeze polypeptides: effects on nucleoside crystal growth. Chem. Commun., 48, 11555-11557.
Wang, S, et al. (2013), Antifreeze Protein-Induced Selective Crystallization of a New Thermodynamically and Kinetically Less Preferred Molecular Crystal. Chem. Eur. J. 19, 16104-16112.
Wang, S, et al. (2014), Molecular Recognition of Methyl aloha-D-Mannobyranoside by Antifreeze (Glyco)Proteins. J. Am. Chem. Soc, 136, 8973-8981.

* cited by examiner

*Primary Examiner* — Amber D Steele
(74) *Attorney, Agent, or Firm* — Andrew D. Fortney; Central California IP Group, P.C.

(57) ABSTRACT

Precipitation of a carbohydrate, such as trehalose, in a solution is prevented by mixing an effective amount of at least one antifreeze protein with the carbohydrate in the solution, wherein the antifreeze protein is in whole or in part one of SEQ ID NO: 1, SEQ ID NO: 2, SEQ ID NO: 3, and SEQ ID NO: 4, and the antifreeze protein mass to the carbohydrate mass is between about 1:8000 and 1:30. The method is especially useful for improving the applications of a carbohydrate, such as trehalose, and the quality of the carbohydrate-containing products in industries by preventing crystallization of the carbohydrate in formulations and products.

20 Claims, 8 Drawing Sheets

Specification includes a Sequence Listing.

SEQUENCE LISTING

```
<160> NUMBER OF SEQ ID NOS: 4

<210> SEQ ID NO 1
<211> LENGTH: 83
<212> TYPE: PRT
<213> ORGANISM: Dendroides canadensis
<220> FEATURE:
<221> NAME/KEY: DAFP1
<222> LOCATION: (1)..(83)
<300> PUBLICATION INFORMATION:
<308> DATABASE ACCESSION NUMBER: GenBank AAB94307.1
<309> DATABASE ENTRY DATE: 1998-01-01
<313> RELEVANT RESIDUES IN SEQ ID NO: (26)..(108)

<400> SEQUENCE: 1

Gln Cys Thr Gly Gly Ser Asp Cys Arg Ser Cys Thr Val Ser Cys Thr
1               5                   10                  15

Asp Cys Gln Asn Cys Pro Asn Ala Arg Thr Ala Cys Thr Arg Ser Ser
            20                  25                  30

Asn Cys Ile Asn Ala Leu Thr Cys Thr Asp Ser Tyr Asp Cys His Asn
        35                  40                  45

Ala Glu Thr Cys Thr Arg Ser Thr Asn Cys Tyr Lys Ala Lys Thr Cys
    50                  55                  60

Thr Gly Ser Thr Asn Cys Tyr Glu Ala Thr Ala Cys Thr Asp Ser Thr
65                  70                  75                  80

Gly Cys Pro

<210> SEQ ID NO 2
<211> LENGTH: 84
<212> TYPE: PRT
<213> ORGANISM: Dendroides canadensis
<220> FEATURE:
<221> NAME/KEY: DAFP2
<222> LOCATION: (1)..(84)
<300> PUBLICATION INFORMATION:
<308> DATABASE ACCESSION NUMBER: GenBank AAB94309.1
<309> DATABASE ENTRY DATE: 1998-01-01
<313> RELEVANT RESIDUES IN SEQ ID NO: (26)..(109)

<400> SEQUENCE: 2
```

```
Gln Cys Thr Gly Gly Ser Asp Cys Arg Ser Cys Thr Val Ser Cys Thr
1               5                   10                  15

Asp Cys Gln Asn Cys Pro Asn Ala Arg Thr Ala Cys Thr Arg Ser Ser
                20                  25                  30

Asn Cys Asn Asn Ala Leu Thr Cys Thr Asp Ser Tyr Asp Cys His Asn
            35                  40                  45

Ala Glu Thr Cys Thr Arg Ser Thr Asn Cys Tyr Lys Ala Lys Thr Cys
        50                  55                  60

Thr Gly Ser Thr Asn Cys Tyr Glu Ala Thr Thr Ala Cys Thr Asp Ser
65                  70                  75                  80

Thr Gly Cys Pro

<210> SEQ ID NO 3
<211> LENGTH: 71
<212> TYPE: PRT
<213> ORGANISM: Dendroides canadensis
<220> FEATURE:
<221> NAME/KEY: DAFP4
<222> LOCATION: (1)..(71)
<300> PUBLICATION INFORMATION:
<308> DATABASE ACCESSION NUMBER: GenBank AAD11275.1
<309> DATABASE ENTRY DATE: 1999-02-01
<313> RELEVANT RESIDUES IN SEQ ID NO: (26)..(96)

<400> SEQUENCE: 3

Gln Cys Thr Gly Gly Ser Asp Cys Gln Ser Cys Thr Val Ser Cys Thr
1               5                   10                  15

Asp Cys Gln Asn Cys Pro Asn Ala Arg Thr Ala Cys Thr Gly Ser Ser
                20                  25                  30

Asn Cys Ile Asn Ala Leu Thr Cys Thr Asp Ser His Asp Cys His Asn
            35                  40                  45

Ala Glu Thr Cys Thr Arg Ser Thr Asn Cys Tyr Lys Ala Lys Thr Cys
        50                  55                  60

Thr Asp Ser Thr Gly Cys Pro
65                  70

<210> SEQ ID NO 4
<211> LENGTH: 71
<212> TYPE: PRT
<213> ORGANISM: Dendroides canadensis
<220> FEATURE:
<221> NAME/KEY: DAFP6
<222> LOCATION: (1)..(71)
<300> PUBLICATION INFORMATION:
<301> AUTHORS: Duman JG, Verleye D, Li N
<302> TITLE: Site-specific forms of antifreeze protein in the beetle
       Dendroides canadensis
<303> JOURNAL: J Comp Phys B
<304> VOLUME: 172
<305> ISSUE: 6
<306> PAGES: 547-52
<307> DATE: 2002-08-01
<313> RELEVANT RESIDUES IN SEQ ID NO: (1)..(71)
<300> PUBLICATION INFORMATION:
<308> DATABASE ACCESSION NUMBER: GenBank AAF86361.1
<309> DATABASE ENTRY DATE: 2000-07-19
<313> RELEVANT RESIDUES IN SEQ ID NO: (21)..(91)

<400> SEQUENCE: 4

Gln Cys Thr Gly Gly Ser Asp Cys Ser Ser Cys Thr Val Ser Cys Thr
1               5                   10                  15

Asn Cys Gln Asn Cys Pro Asn Ala Arg Val Ala Cys Thr Gly Ser Thr
                20                  25                  30
```

```
Asn Cys Ile Asn Ala Leu Thr Cys Thr Asp Ser His Asp Cys His Asn
            35                  40                  45

Ala Glu Thr Cys Thr Arg Ser Thr Asn Cys Tyr Lys Ala Lys Thr Cys
    50                  55                  60

Thr Asp Ser Thr Gly Cys Pro
65                  70
```

METHOD OF PREVENTING CARBOHYDRATE CRYSTALLIZATION

This application claims the benefit of U.S. Provisional Patent Application No. 62/132,398, filed on Mar. 12, 2015.

BACKGROUND

Temperatures below the freezing point of water —0 degrees Celsius, otherwise described as −32 degrees Fahrenheit—cause liquid water to turn solid. Since living organisms are comprised mostly of liquid water, the exposure to external temperatures below the freezing point is dangerous. After lengthy exposure to a below freezing temperature, the liquids within the body will begin to solidify and damage the biological cells. Also, in nature, physiological solutes whose solubilities change dramatically with temperature changes may crystallize or solidify in body fluids, which can be lethal. This may damage the organism and lead to death of the organism.

Trehalose is a multifunctional non-reducing disaccharide, occurring naturally in all biological kingdoms. In addition to being an energy and carbon source, this sugar protects cells and proteins against injuries in extreme environments, prevents osteoporosis, alleviates certain diseases, and acts as a signal molecule in plants. Due to its superior bioprotective properties, trehalose has a wide range of applications in industries (e.g., medical, pharmaceutical, and food industries). For examples, trehalose can be used as an additive in foods to maintain moisture and/or the stabilities of other food components; trehalose can be included in formulations of drugs and vaccines to pertain the stability and functions of active pharmaceutical ingredients; trehalose can also be used as a cryoprotectant.

However, the solubility of trehalose decreases dramatically with the decrease of temperature and its hydrate has even lower solubility than trehalose. Thus, trehalose is prone to precipitation or crystallization out of the solutions or formulations, in particular, at low temperatures, to form trehalose dihydrate. Trehalose's high propensity to precipitation or crystallization significantly limits its applications as such precipitation/crystallization can greatly impair the protection effectiveness of trehalose as well as the quality of the final products. Therefore, an effective and environmentally friendly additive for preventing trehalose precipitation/crystallization is needed.

Antifreeze Proteins ("AFP's") in cold-adapted organisms including fish, insects, plants, bacteria, fungi bind to specific surfaces of ice crystals to inhibit their growth of ice in vivo. AFPs depress the freezing point of water without appreciably altering the melting point leading to a difference between the melting point and the freezing point, referred to as thermal hysteresis (TH, a measure of antifreeze activity). AFPs in freeze-avoiding species prevent them freezing. However, AFPs are also present in freeze-tolerant species at levels too low to produce significant antifreeze activity, causing speculation of their role in freeze-tolerant species. More recently, AFPs role in controlling the formation of other types of crystals, such as nucleosides, has been also reported.

SUMMARY OF THE INVENTION

The present invention includes a method of preventing precipitation of a carbohydrate in a solution, having the following steps: taking a solution containing the carbohydrate, then mixing an effective amount of at least one antifreeze protein with the carbohydrate in the solution, wherein the antifreeze protein is described in one of SEQ ID NO: 1, SEQ ID NO: 2, SEQ ID NO: 3, and SEQ ID NO: 4, and wherein a ratio of the antifreeze protein mass to the carbohydrate mass is between about 1:8000 and about 1:30.

In one aspect of the invention, the carbohydrate may be a disaccharide, and in certain embodiments may be a disaccharide of glucose, and in specific embodiments may be trehalose.

In one aspect of the invention, the antifreeze protein may consist of the protein described in SEQ ID NO: 1. In a second aspect of the invention, the antifreeze protein may consist of the protein described in SEQ ID NO: 2. In a third aspect of the invention, the antifreeze protein may consist of the protein described in SEQ ID NO: 3. In a fourth aspect of the invention, the antifreeze protein may consist of the protein described in SEQ ID NO: 4. In yet another aspect of the invention, the mixing step of the method includes adding an effective amount of at least two antifreeze proteins, wherein each one of the two added antifreeze proteins is described in one of: SEQ ID NO: 1, SEQ ID NO: 2, SEQ ID NO: 3, and SEQ ID NO: 4.

The present inventions also includes a method of enhancing the thermal hysteresis of an antifreeze protein in a solution by at least 10%, comprising adding an effective amount of a trehalose to the solution, wherein the antifreeze protein and the trehalose are both at a physiological concentration, and wherein the antifreeze protein is described in one of: SEQ ID NO: 1, SEQ ID NO: 2, SEQ ID NO: 3, and SEQ ID NO: 4. In one aspect of the method of enhancing thermal hysteresis, the antifreeze protein has an antifreeze protein concentration and the effective amount has a trehalose concentration, and the antifreeze protein concentration is between about 1 mg/mL and about 3 mg/mL and the trehalose concentration is between about 30 mg/mL and about 400 mg/mL.

In yet another aspect of the invention, a method of preventing precipitation of a carbohydrate in a solution includes taking a solution containing the carbohydrate, mixing an effective amount of at least one antifreeze protein with the carbohydrate in the solution, wherein the antifreeze protein has a residue sequence, and the residue sequence is about 10% identical to a residue sequence in one of SEQ ID NO: 1, SEQ ID NO: 2, SEQ ID NO: 3, and SEQ ID NO: 4, and wherein a ratio of the antifreeze protein mass to the carbohydrate mass is between about 1:8000 and about 1:30.

In another aspect of the invention, the antifreeze protein may be selected from the group consisting of natural or engineered antifreeze proteins, antifreeze polypeptides and antifreeze peptides, active fragments of antifreeze proteins, antifreeze polypeptides and antifreeze peptides, mimetics of antifreeze proteins, antifreeze polypeptides and antifreeze peptides, their active mimetic fragments, and combinations thereof.

BRIEF DESCRIPTION OF THE PREFERRED EMBODIMENTS

Figure 1A:
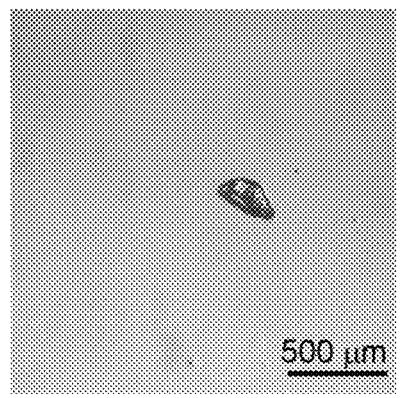
FIG. 1A is an image that shows the presence of precipitation of crystalline trehalose when the aqueous solution of trehalose at about 30 mg/mL was cooled from room temperature to −5° C. and annealed at −5° C. for 2 hours.

Administering a solution of carbohydrate and antifreeze protein(s) to living organisms may prevent the organisms from expiring in extremely cold temperatures. Examples of carbohydrates include, but are not limited to monosaccharides, disaccharides, trisaccharides, and water (or alcohol) soluble multisaccharides. For example, carbohydrates may be sugars or their derivatives (trehalose, glucose, fructose, sucrose, lactose, maltose, galactose, 2-deoxy-galactose, methyl-D-mannoside, mannose, mannitol, sorbitol, xylitol, glycerol, nucleosides, D-(+)-melibose, and D-(+)-raffinose). The antifreeze protein may be selected from the group consisting of natural or engineered antifreeze proteins, antifreeze polypeptides and antifreeze peptides, active fragments of antifreeze proteins, antifreeze polypeptides and antifreeze peptides, mimetics of antifreeze proteins, antifreeze polypeptides and antifreeze peptides, their active mimetic fragments, and combinations thereof.

Administering trehalose and antifreeze protein is effective at preventing living organisms from expiring in sub-freezing temperatures. The structure of trehalose is:

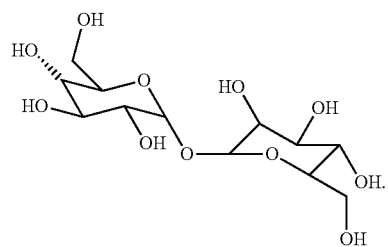

The antifreeze protein used in the solution with a carbohydrate—preferably trehalose—may be any biological antifreeze protein found in living organisms. Specifically, the antifreeze protein may be any one *Dendroides canadensis* antifreeze protein (DAFP) isomers.

DAFP-1 has a molecular weight of 8.7 kDa and is represented by

```
                                      SEQ ID NO: 1
QCTGGSD CRSCTVSCTD CQNCPNARTA CTRSSNCINA
LTCTDSYDCH NAETCTRSTN CYKAKTCTGS TNCYEATACT
DSTGCP.
```

DAFP-2 has a molecular weight of 8.8 kDa and is represented by

```
                                      SEQ ID NO: 2
QCTGGSD CRSCTVSCTD CQNCPNARTA CTRSSNCNNA
LTCTDSYDCH NAETCTRSTN CYKAKTCTGS TNCYEATTAC
TDSTGCP.
```

DAFP-4 has a molecular weight of 7.3 kDa and is represented by

SEQ ID NO: 3
QCTGGSD CQSCTVSCTD CQNCPNARTA CTGSSNCINA
LTCTDSHDCH NAETCTRSTN CYKAKTCTDS TGCP.

DAFP-6 has a molecular weight of 7.3kDa and is represented by

QCTGGSD CSSCTVSCTN CQNCPNARVA CTGSTNCINA
LTCTDSHDCH NAETCTRSTN CYKAKTCTDS TGCP.

Experiments validating the present invention were carried out in larvae of the beetle *Dendroides canadensis* which spend the winters under the loose bark of partially decomposed hardwood logs. As described in Experiments 1 and 2 below, trehalose and AFPs work in cooperation to provide organisms with the ability to survive extremely cold temperatures. Trehalose and AFPs can be administered to living organisms to increase their ability to survive in extreme cold temperatures.

To help living organisms survive extreme temperatures—specifically, extremely cold temperatures—an effective amount of trehalose and an effective amount of antifreeze protein can be administered together in vivo, administered directly into a body fluid stream, such as blood, gut fluid, and/or urine. A way to administer an effective amount of trehalose and an effective amount of antifreeze protein together would be to create a solution and then to administer the solution to living organisms.

Creating the solution containing an effective amount of trehalose and an effective amount of antifreeze protein may be accomplished by one of—or a combination of—the following ways: 1) adding a stock solution containing trehalose and a stock solution containing antifreeze proteins at a certain ratio of antifreeze protein to trehalose into a liquid containing water; 2) adding solids containing trehalose and solids containing antifreeze proteins at a certain ratio of antifreeze protein to trehalose into a liquid containing water; and 3) adding solids/liquids containing trehalose and solids/liquids containing antifreeze proteins at a certain ratio of antifreeze protein to trehalose into a system containing liquid water.

For example, 175 mg of trehalose and 1 mg of DAFP-1 can be dissolved in 1 mL of 0.9% preservative-free sodium chloride at room temperature. This will create a solution that has molar ratio of DAFP-1 trehalose $2 \times 10^{-4}$. The prepared solutions can be sterilized using a sterilized syringe filter. The sterilized sample can be stored at room temperature for days. Alternatively, the prepared solutions can be stored at 4° C. for weeks or stored at −20° C. for months. The prepared solutions can also be lyophilized, and the resulting powders can be stored for years.

A method to introduce this solution into the blood stream of a living organism would be best administered via injection, subcutaneously or intravenously. The injection may involve reconstituting a previously lyophilized sample of trehalose and antifreeze protein at a certain ratio using saline or some other pharmaceutically acceptable diluent. For example, we can intravenously inject the diluted trehalose-antifreeze protein solution to animals that need such cold protection and the final blood will contain between about 15 mg/mL and about 30 mg/mL trehalose and between about 0.5 mg/mL and about 1 mg/mL of antifreeze protein.

A method to introduce this solution into the gut fluid of a living organism would be administered via injection into the gut fluid or the blood stream, or via ingestion, whether eaten or drank, depending on the organisms. A method to introduce this solution into the urine stream of a living organism would be administered via injection into the urine stream or the blood stream or via ingestion, whether eaten or drank, depending on the organisms.

Also, an effective amount of trehalose and an effective amount of antifreeze protein can be administered in vitro, added directly into a solution in contact with a living organism or added directly into samples including tissues, cells, proteins, nucleic acids, active pharmaceutical ingredients (APIs), and sugars. Methods of in vitro administration may include: adding the prepared solutions as described above or alternatively by adding the stock solutions of trehalose and antifreeze proteins, respectively, into a biological sample that need to be preserved at cold temperatures for a long term. This administration can be performed at room temperature. The final concentration of trehalose present in the sample can be as low as about 10 mg/mL or as high as 680 mg/mL and the final concentration of antifreeze protein present in the sample can be as low as 2 µg/mL or as high as 10 mg/mL.

The sample exposed to and preserved by the trehalose-antifreeze protein solution can then be stored for an extended time under extremely cold conditions. The trehalose-antifreeze protein can be used in association with freeze-drying and lyophilizing to better protect and preserve the sample.

An effective molar ratio of antifreeze protein to trehalose in a solution to be administered in vitro may be between about $0.5 \times 10^{-5}$ and about $3 \times 10^{-2}$, preferably between about $2 \times 10^{-5}$ and about $7 \times 10^{-4}$, and most preferably about $4 \times 10^{-5}$. Another way to express the molar measurement ratio of antifreeze protein to trehalose in solution may between about 1:200,000 and about 1:1,000, preferably between about 1:50,000 and about 1:1,400, and most preferably about 1:25,000.

Also, an effective amount of antifreeze protein can be added into trehalose containing samples or formulations (e.g., trehalose syrup, trehalose containing freeze-drying formulations) to prevent the crystallization of trehalose during various processes (e.g., pre-production, production, and post-production). An effective weight ratio of the antifreeze protein to the carbohydrate is between about 1:8000 and about 1:30.

EXPERIMENT 1: BEETLE LARVAE CONTAIN HIGHER AMOUNTS OF TREHALOSE IN WINTER MONTHS THAN IN SUMMER MONTHS

To establish quantitatively the amount of trehalose in *D. canadensis* hemolymph, we first collected the winter and summer hemolymphs of the beetle and determined the concentrations of trehalose in the hemolymphs using trehalose. The level of trehalose was determined to be 29.6 mg/mL or 0.09 M in the winter hemolymph of *D. canadensis*, which is within the reported amounts of trehalose, ranging from 0.02 M to 0.17 M, in a great number of insects.

Figure 1B:
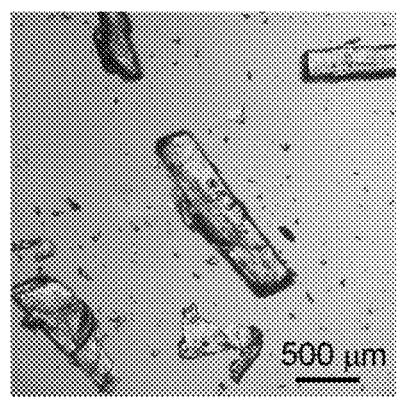
FIG. 1B is an image that shows the precipitated trehalose crystals increasing the amounts (in both size and number) in the aqueous solution of trehalose at about 30 mg/mL was continuously cooled from −5° C. to −10° C. and annealed at −10° C. for 2 hours.
Figure 1C:
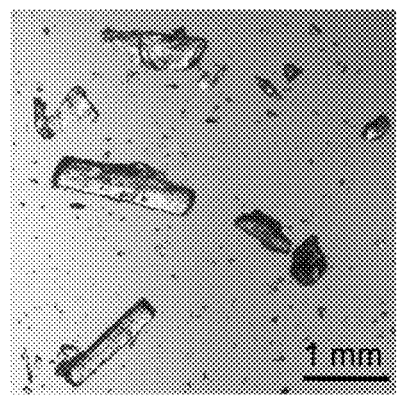
FIG. 1C is an image that shows the precipitated trehalose crystals increasing the amounts (in both size and number) in the aqueous solution of trehalose at about 30 mg/mL as the solution was continuously cooled from 10° C. to −15° C. and annealed at −15° C. for 2 hours.

In contrast, the level of trehalose decreased dramatically to less than 0.1 mg/mL in the summer hemolymph of *D. canadensis*. It is known that the solubility of trehalose in water changes dramatically with temperature and is low at low temperatures. When its solutions experience low temperature fluctuations, trehalose is prone to crystallize. We showed that cooled aqueous solution with 29.6 mg/mL of trehalose from room temperature to −5° C. and annealing it at −5° C. for 2 hours leads to the precipitation of crystalline trehalose (FIG. 1A). The sizes of these trehalose crystals increased continuously as the temperature fell to −10 and −15° C. (FIGS. 1B and 1C).

Materials. All chemicals or better were purchased from Sigma-Aldrich (St. Louis, Mo.) at ACS grade and were used without additional purification. HPLC grade solvents and chemicals were purchased from Sigma-Aldrich. All of the aqueous solutions were prepared using Milli-Q water produced from a Synergy water system (Millipore) with a minimum resistivity of 18 MΩ·cm. All of the samples including the protein samples were filtered through 0.2 μm filters before use unless otherwise indicated. 8 mL sample vials (National Scientific) were used for crystallization. All glassware and stir bars were first cleaned in a KOH/2-propanol bath. After rinsing with distilled water, the glassware and stir bars were soaked in 1 M HCl for 24 h and then rinsed with distilled water. Finally they were cleaned using RBS35 (Pierce), a surface-active detergent. After rinsing with distilled water and then with deionized water, the glassware and stir bars were air dried at room temperature before use.

Preparation of D. canadensis hemolymph. Larvae were collected in the field from wooded areas in the vicinity of South Bend, Indiana (northern Indiana and southern Michigan) in both summer (July) and winter (January). Larvae were kept at field temperatures and immediately transported to the laboratory at the University of Notre Dame, where hemolymph was extracted from individual larvae by puncturing the cuticle in the dorsal midline with a 30 gauge needle and collecting the hemolymph (~2-8 μL per individual) in a 10 μL glass capillary tube via capillary action. Hemolymph was pooled and stored at −80° C.

Determination of the levels of trehalose in the hemolymph of Dendroides canadensis. The amount of trehalose in the hemolymph of Dendroides canadensis was determined using a modified method. The hemolymph, 5 μL, was placed in a polyethylene centrifuge tube containing 195 μL 0.25 M $Na_2CO_3$. The sample was vortexed for 2 minutes and then incubated at 100° C. for 3 h to inactivate all enzymes in the hemolymph and to convert glucose, if any, into its reductive form. The pH of the sample was adjusted to 5.70 by adding 960 μL of 1 M acetic acid and 3.84 mL 0.25 M sodium acetate. The sample was then centrifuged at 12,000 rpm at 25° C. for 10 minutes. To fully convert trehalose in the hemolymph into glucose, 100 μL of the supernatant was incubated overnight at 37° C. with 2 μL porcine kidney trehalase (Sigma, T8778). The amount of glucose in 46 μL of the treated supernatant was measured using the Glucose Assay Kit (Sigma, GAGO20). The glucose concentration was corrected by deducting the amount of glucose present in the supernatant before trehalase treatment. The trehalose concentration for D. canadensis winter hemolymph was determined to be 29.58 mg/mL, which is within the range of the known amount of trehalose in beetles.

EXPERIMENT 2: AFP'S PREVENT PRECIPITATION/CRYSTALLIZATION OF TREHALOSE

The hemolymph of the overwintering larvae of D. canadensis contains four AFP isomers (DAFP-1, DAFP-2, DAFP-4, and DAFP-6) with molecular weights ranging from 7.3 kDa-8.9 kDa. The level of the hemolymph AFPs are elevated in winter (1.6 mg/mL-2.6 mg/mL), resulting in high antifreeze activity, while the level of hemolymph AFPs in summer is too low to be measured. The antifreeze activity of pure DAFP-1 is reported to be further enhanced by trehalose at a concentration of 0.25 M or higher.

The overwintering larvae of D. canadensis also produce AFPs from a family of some 30 AFP isomers that are differentially expressed in various tissues and body fluids (hemolymph, gut, urine and epidermal cells). The combination of antifreezes permits the larvae to inhibit lethal freezing above temperatures of approximately −18° C. to −28° C., depending on the severity of the winter. The AFP's consist of 12-mer and 13-mer repeating units containing highly conserved threonine and cysteine residues that form right-handed β-helices resulting in the flat ice-binding site on one side of the β-barrel.

Figure 1D:
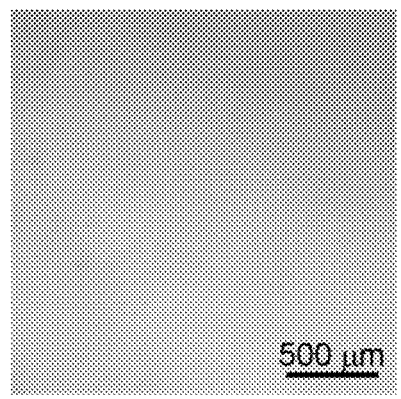
FIG. 1D is an image that shows no precipitated trehalose when both trehalose and AFPs are present in beetle hemolymph when the hemolymph sample was cooled from room temperature to −5° C. and annealed at −5° C. for 2 hours.
Figure 1E:
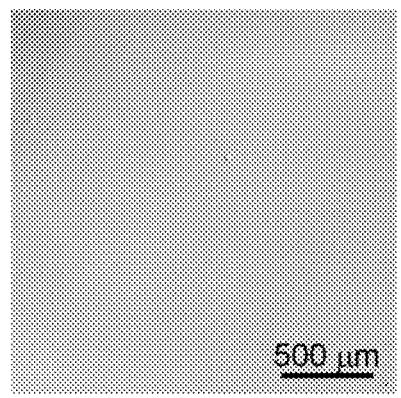
FIG. 1E is an image that shows no precipitated trehalose when both trehalose and AFP's are present in beetle hemolymph when the hemolymph sample was continuously cooled from −5° C. to −10° C. and annealed at −10° C. for 2 hours.
Figure 1F:
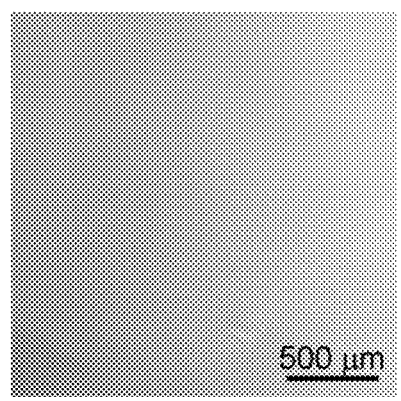
FIG. 1F is an image that shows no precipitated trehalose when both trehalose and AFP's are present in beetle hemolymph when the hemolymph sample was continuously cooled from −10° C. to −15° C. and annealed at −15° C. for 2 hours.

To demonstrate whether precipitates appear in the winter hemolymph of D. canadensis, where both trehalose and AFP's are present, we cooled and annealed the hemolymph sample to −5° C., −10° C., and −15° C. As expected, no precipitates were observed (FIGS. 1D, 1E and 1F).

Figure 1G:
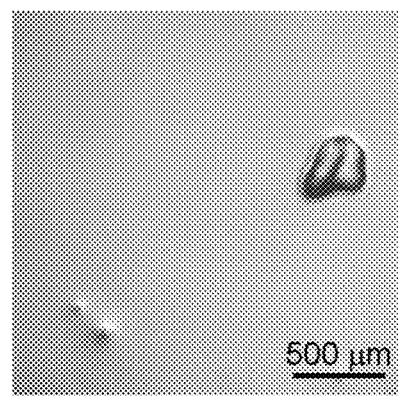
FIG. 1G is an image that shows the presence of precipitated trehalose in AFP-free hemolymph (i.e., AFPs were removed from the hemolymph sample) when the AFP-free hemolymph was cooled from room temperature to −5° C. and annealed at −5° C. for 2 hours.
Figure 1H:
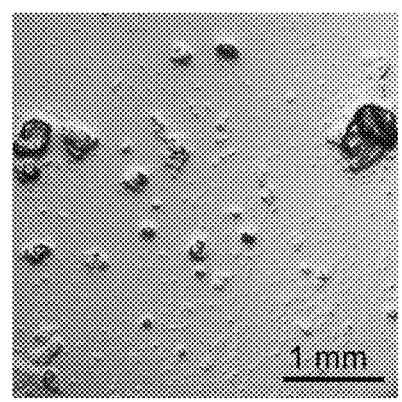
FIG. 1H is an image that shows the precipitated trehalose in AFP-free hemolymph increasing the amounts (in both size and number) when the AFP-free hemolymph sample was continuously cooled from −5° C. to −10° C. and annealed at −10° C. for 2 hours.
Figure 1I:
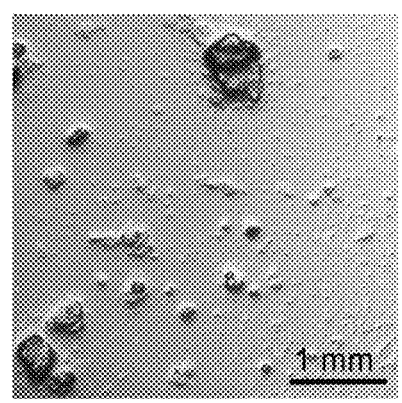
FIG. 1I is an image that shows the presence of precipitated trehalose in AFP-free hemolymph increasing the amounts (in both size and number) when the AFP-free hemolymph sample was continuously cooled from −10° C. to −15° C. and annealed at −15° C. for 2 hours.
Figure 1J:
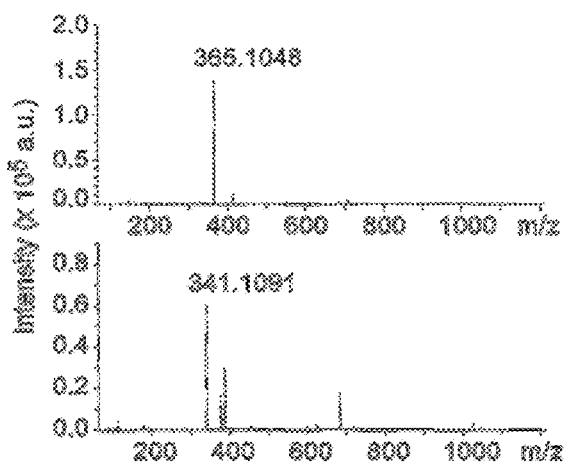
FIG. 1J is an LC-MS spectrometry image confirming that the final crystalline precipitates in FIG. 1I were pure trehalose.
Figure 1K:
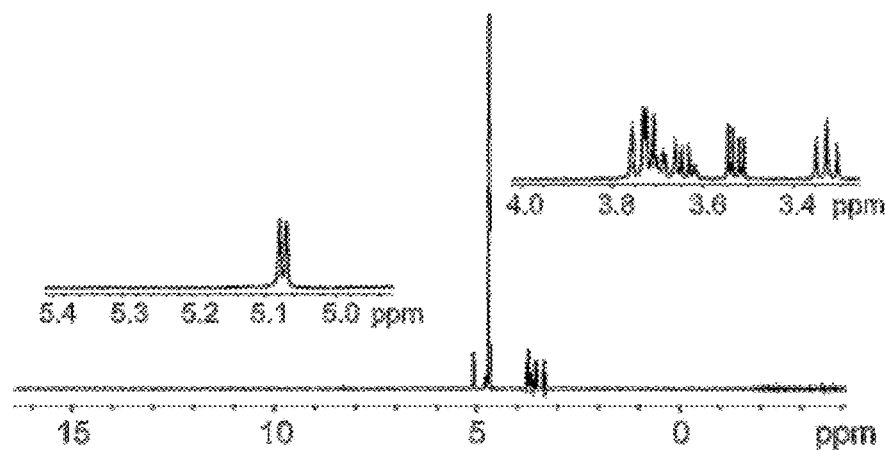
FIG. 1K is an NMR ($^1$H) spectroscopy image confirming that the final crystalline precipitates in FIG. 1I were pure trehalose.
Figure 1L:
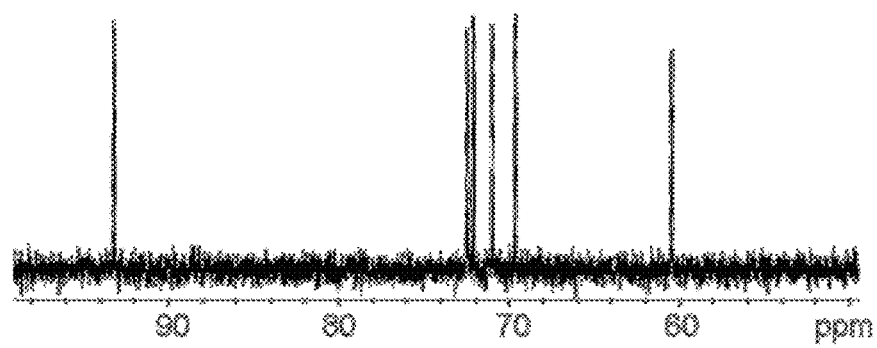
FIG. 1L is an NMR ($^{13}$C) spectroscopy image confirming that the final crystalline precipitates in FIG. 1I were pure trehalose.

To explore the links between the inhibition of trehalose crystallization and the existence of AFPs, we removed AFPs from the winter hemolymph of D. canadensis and performed similar experiments on the AFPs free hemolymph. In contrast to normal hemolymph containing AFPs, crystalline precipitates appeared at −5° C. in the AFP-free hemolymph (FIG. 1G) and the sizes of the precipitates increased when the temperature was lowered to −10° C. and −15° C. (FIGS. 1H and 1I). These precipitates were characterized using LC-MS spectrometry and NMR ($^1$H and C) spectroscopy and the results confirmed that the crystalline precipitates were pure trehalose (FIGS. 1J, 1K and 1L).

To validate that AFPs are required for inhibiting trehalose crystallization in the hemolymph, we added purified DAFP-1 at 1.0 mg/mL (an abundant AFP isoform at a physiological concentration on the lower end in the winter hemolymph of D. canadensis) back to the AFP-free hemolymph. No precipitates appeared in the AFP-added hemolymphs when the samples were cooled and annealed at −15° C. Moreover, we added purified AFP at 1.0 mg/mL to a trehalose aqueous solution (29.6 mg/mL). No precipitates appeared in the AFP added trehalose solutions when the sample solutions were cooled and annealed at −15° C. Trehalose precipitation and trehalose crystallization were completely inhibited by the addition of the AFP to trehalose-containing samples at the ratio of AFP mass (or weight) to trehalose mass (or weight) of about 1:30.

We denatured purified DAFP-1 by disruption of its tertiary structure and used the denatured AFP as a control. In contrast, the addition of denatured AFP at the same or higher concentrations, such as 3.0 mg/mL, to the AFP's free hemolymph and to the trehalose solution, failed to show its ability of inhibition the precipitation of crystalline trehalose that were observed in these samples at −5° C.

Methods. The sizes of winter hemolymph AFP isomers are between 7 kDa and 9 kDa. Forty μL of winter hemolymph was diluted to 200 μL by adding 160 μL of double deionized water. A 100 μL aliquot of the diluted hemolymph was passed through the Nanosep Centrifugal Devices (Pall Corporation, MWCO 3K) and the filtrate, which yielded a filtrate free of hemolymph macromolecules including AFP's, was saved for use. A second 100 μL aliquot of the diluted hemolymph portion of the hemolymph was passed through Nanosep Centrifugal Devices (Pall Corporation, MWCO 10K) and the samples on the ultrafiltration membrane and in the sample reservoir, if any, were recovered and saved for use. The two saved samples were combined and lyophilized. The lyophilized sample was then solubilized in 40 μL deionized water, yielding an AFP's-free hemolymph sample. Forty microliters of the following samples, native winter beetle hemolymph (vial 1), the AFP's-free hemolymph sample (vial 2), and a 29.6 mg/mL trehalose aqueous solution (vial 3, a control), were placed in three vials, respectively. The sample vials were then placed into the center of aluminum blocks of a bench top hot/cold block incubator (TropiCooler, Boekel Scientific). The temperature was cooled from room temperature to −5° C. and held for 2 hours. Images were then taken for the samples at −5° C. The temperature was then cooled to −10° C. and held for 2 hours. Images were then taken for the samples at −10° C. The temperature was then cooled to −15° C. and held for 2 hours. Images were then taken for the samples at −15° C. The cooling rate was 1° C./minute for the above experiments. The solids that appeared in vial 2 were collected and washed three times with cold 70% (v/v) ethanol-water solution at −20° C. The solid samples were held under vacuum for 24 hours.

Figure 2A:
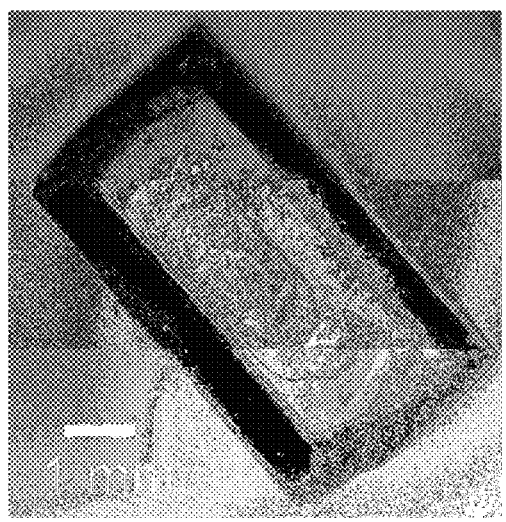
FIG. 2A is an image that shows well-formed trehalose dihydrate crystals in the absence of AFPs.
Figure 2B:
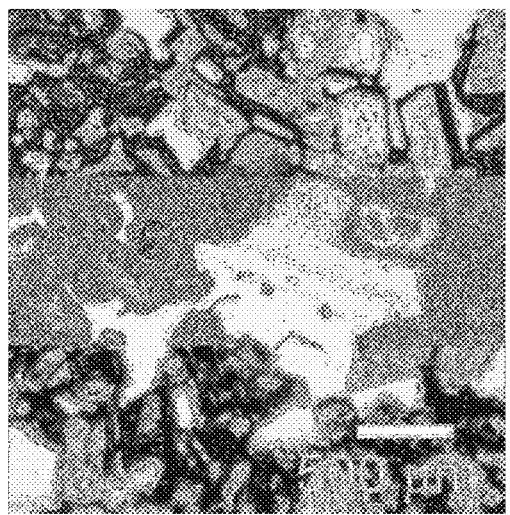
FIG. 2B is an image showing that the presence of the AFP at 0.04 mg/mL significantly delays and inhibits trehalose crystallization for at least 2 days and the finally achieved trehalose dihydrate crystals have much smaller sizes and amounts.
Figure 3A:
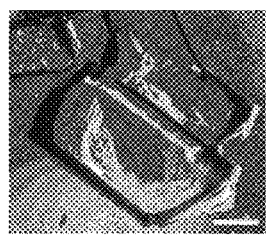
FIG. 3A is an image that shows trehalose dihydrate crystals obtained in the presence of the denatured AFP at 1.1 mg/mL as a negative control. The length of the scale bars is 500 μm.
Figure 3B:
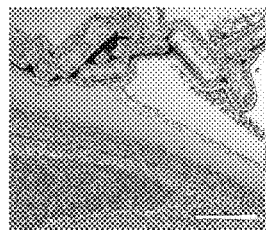
FIG. 3B is an image that shows trehalose dihydrate crystals obtained in the presence of the AFP at 0.1 mg/mL. The length of the scale bars is 500 μm.
Figure 3C:
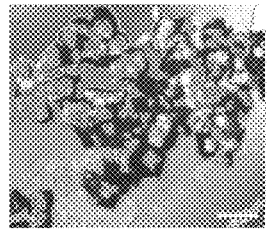
FIG. 3C is an image that shows trehalose dihydrate crystals obtained in the presence of the AFP at 0.8 mg/mL. The length of the scale bars is 500 μm.

To further understand the effect of AFP's preventive role on trehalose precipitation or crystallization, we investigated DAFP-1 as an additive at various concentrations (i.e., resulting in a wide range of AFP:trehalose ratios). We compared trehalose crystallization processes in the absence and presence of the AFP additive. The presence of the AFP at all testing concentrations significantly delayed or inhibited trehalose crystallization. In the absence of AFPs, trehalose first precipitated from the trehalose solution on day 4 (Table 1). The addition of the AFP at the final sample concentration of 5 μM (or 0.04 mg/mL), i.e., at an AFP molarity to trehalose molarity ratio of about $4 \times 10^{-5}$ or an AFP mass to trehalose mass ratio of about 1000, completely prevents the precipitation or crystallization of trehalose for at least 2 days (Table 1). With the addition of AFP at the concentration of 0.04 mg/mL, no precipitation of trehalose was observed until day 6 (Table 1). The higher the AFP concentration (or ratio of AFP to trehalose), the more significant prolonged duration the inhibition/prevention was (Table 1). The experiments were stopped on day 21, and the weights of the finally achieved trehalose crystals were then measured. Moreover, in the presence of AFPs, much less amounts (in both size and weight) of trehalose precipitates were achieved (Table 1). The resulting trehalose crystals in the AFP containing trehalose samples are much smaller (FIGS. 2b, 3b and 3c and Table 1). The higher the concentrations of the AFP, the more pronounced were the precipitation prevention effects on the carbohydrate, in this case trehalose (FIGS. 1d-f, 2b, 3b, 3c; Table 1). By adding different concentrations of DAFP-1 to a solution containing trehalose, the trehalose precipitation and crystallization can be carefully controlled by time and amount.

The crystals from these studies were confirmed to be trehalose dihydrate by single crystal X-ray diffraction (Table 2), although the amounts and sizes of the crystals from the trehalose solutions in the absence and presence of the AFP were different.

Figure 2C:
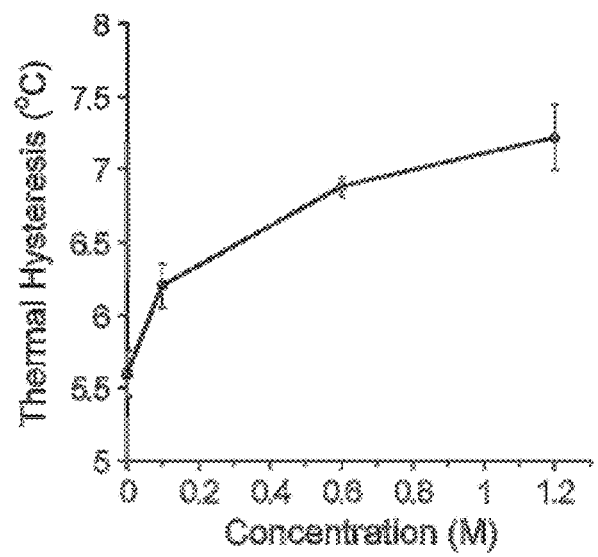
FIG. 2C is a graph that shows that the TH of the AFP at a physiological concentration of 1 mg/mL was assessed to be 5.59° C., which is enhanced approximately 11% (or 6.20° C.) by trehlaose alone at a physiological concentration of 0.1 M.

We also assessed the effect of trehalose on the thermal hysteresis (TH) of DAFP-1 at physiological concentrations. The TH of DAFP-1 at a physiological concentration of 1 mg/mL was assessed to be 5.59° C., which was enhanced at least 10% (or 6.15° C.), or approximately 11% (or 6.20° C.) by trehalose at a physiological concentration of 0.1 M (FIG. 2C), suggesting that trehalose also functions as a physiological antifreeze activity enhancer in the winter hemolymph.

The internal temperature of certain ectothermic organisms (e.g., fish, insects) depends on the environmental temperature and varies dramatically upon the change of the environmental temperature. Certain physiological solutes in their bodily fluids are sensitive to these temperature changes, the precipitations of which are lethal. Consequently, effective mechanism(s) to prevent such phase transition of these solutes in poikilothermic organisms should present. This work is a prime example of this endeavor. Our work provides new evidence that the presence of high levels of trehalose in conjunction with inhibition of trehalose crystallization at such levels is essential for insect cold survival. We have shown that the presence of the AFPs in the winter hemolymph of D. canadensis is essential to prevent trehalose precipitation at these high levels under fluctuating low temperatures.

The hemolymph AFPs share structural similarities with the other AFPs in D. canadensis, the AFPs of Tenebrio molitor and other beetle AFPs, suggesting similar roles of these AFPs in inhibiting the precipitations of certain co-solutes from the bodily fluids. Our work reveals a significant synergistic relationship between trehalose and AFPs in cold protection, suggesting a new role for AFPs. This new role for AFPs in preventing trehalose precipitation and crystallization provides new approaches toward designing cryoprotective systems and new, improved industrial uses for trehalose (e.g., pharmaceutical, medical, and food).

Mass Spectrometry. Mass spectra of the solid samples were obtained using a Waters 2795 HPLC system with ZQ single quadrupole MS and an electrospray ionization source. Samples were introduced using loop injection. The results of the mass spectra of the vial 2 sample are shown as the following: positive ESI, m/z: $[M+Na]^+$ calcd. for $C_{12}H_{22}O_{11}Na$, 365.33; found 365.11; negative ESI, m/z: $[M-H]^-$ calcd. for $C_{12}H_{22}O_{11}Na$, 341.33; found 341.11.

NMR Spectroscopy. Bruker 400 NMR spectrometry was used to acquire $^1H$ NMR ($D_2O$, 400 NMR) and $^{13}C$ NMR ($D_2O$, 100.6 NMR). The $^1H$ and $^{13}C$ NMR spectra of the sample in vial 2 are identical to the standard spectra of d-trehalose dihydrate deposited in biological magnetic resonance data bank (BMSE 000125).

Crystal growth procedure. Trehalose can be crystallized (dihydrate form) from pyridine or aqueous solutions of ethanol by evaporation. However, we found that the single crystal yield was low (30% from pyridine-ethanol solutions, and 5% from aqueous ethanol solutions). Here, we crystallized trehalose dihydrate crystals by diffusing ethanol into the aqueous ethanol solution of trehalose directly. D-(+)-trehalose, 0.429 g, was dissolved into 3.30 mL water at 29° C., and then 6.6 mL of anhydrous ethanol was added. On day 1, each sample vial was weighed and 900 μL of the above alcoholic trehalose solution was added. Then 3 μL of water or protein solutions at certain concentrations were added into each vial. The vials were gently swirled after the addition and were transferred into a big jar containing ethanol to a depth of about 2 cm. The final trehalose concentration was 125 mM in each vial, and the protein/trehalose molar ratios ($\times 10^{-4}$) were varied (0, 0.05, 0.5, 1.2, 1.5, 7.2, and 9.0). The cover of the jar was closed tightly, and the jar was held at 4° C. Each vial was checked for crystals every 8 hours until crystals appeared. The solution in each vial was then removed. After the vials were dried in the air, the weight for each vial with the crystals was recorded. The experiments were repeated five times. The single crystal yield was 100% using the diffusion method. Sample results are listed in Table 1. Photos of the vials were taken with a Canon EOS 30D camera during and at the end of the crystallization process, and again when the process finished (data are not shown). Optical micrographs were taken under a Nikon SMZ800 microscope with a Nikon Coolpix 5400 when the crystallization was completed.

Thermal hysteresis measurements. Freezing and melting points were determined in aqueous samples using a Clifton nanolitre osmometer (Clifton Technical Physics) following a previously reported protocol. The instrument was calibrated with distilled water (0 mOsm) and a 1000 mOsm NaCl standard (Optimole, Wescor Inc.). Samples were suspended in heavy immersion oil. They were cooled until frozen, and then slowly warmed until a single ice crystal (approximately 15 μm-20 μm) slowly melted while observed at 200×. This temperature was taken as the melting point or equilibrium freezing point. Following determination of the melting point, a 10 μm single ice crystal was slowly cooled to 0.18° C. below the melting point, held for 1 min, and then cooled to 1.8° C. below the melting point and held for a minute, then to 3.6° C. below the melting point and held for a minute, then to 5.4° C. below the melting point and then to −6° C. and held for 30 minutes. They were then cooled at 0.074° C. per minute until sudden rapid growth was observed, and this value was taken as the freezing point. Melting and freezing point determinations for each sample were repeated at least three times. The thermal hysteresis, the difference between the melting point and the freezing point, represents the antifreeze activity.

Single Crystal X-ray Diffraction. Crystals were sent to X-ray crystallography facility at California Institute of Technology for analysis. Data were collected at 100.15 K with a Bruker APEX II CCD using Mo K alpha radiation. Non-hydrogen atoms were refined anisotropically by full matrix least-squares on $F^2$. The crystallographic data of trehalose dihydrate crystals grown in the presence of the AFP was reported in Table 2.

TABLE 1

Sample results for trehalose dihydrate crystal growth in the presence or absence of the AFP and denatured AFP (used as control).

| Sample[a] | AFP concentration (mg/mL) | Induction time (day)[b] | Weight of Crystals (mg) |
|---|---|---|---|
| Trehalose | 0 | 4 | 37.4 |
| Trehalose + control | 1.1 | 4 | 37.5 |
| Trehalose + AFP | 0.04 | 6 | 28.2 |
| Trehalose + AFP | 0.1 | 8 | 17.9 |
| Trehalose + AFP | 0.8 | 8 | 15.6 |

[a]Each sample contained 42.8 mg/mL trehalose on day 1 and the experiments were stopped on day 21. Results of trehalose alone and in the presence of control (i.e., denatured DAFP-1) were listed for comparison.
[b]The day that the first appearance of solid was observed.

TABLE 2

Crystallographic Data for Trehalose Dihydrate

| Formula | $C_{12}H_{22}O_{11} \cdot 2H_2O$ |
|---|---|
| Formula Weight | 378.33 |
| Data collection temperature | 100.15K |
| Crystal system | orthorhombic |
| Space group | $P2_12_12_1$ |
| Unit cell dimensions | |
| a, b, c (Å) | 7.5341(4), 12.1764(7), 17.7886(10) |
| α, β, γ (°) | 90°, 90°, 90° |
| Volume | 1631.89(16) Å$^3$ |
| Z | 4 |
| Density (calculated) | 1.540 g/cm$^3$ |
| Reflections > 2 σ (I) | 15934 |
| Average σ (I)/(net I) | 0.0299 |
| Data/restraints/parameters | 17593/0/330 |
| Final R indices [I > 2 σ (I)] | $R_1$ = 0.0312, $wR_2$ = 0.0596 |
| R indices (all data) | $R_1$ = 0.0379, $wR_2$ = 0.0602 |

EXPERIMENT 3: STUDYING THE INTERACTIONS BETWEEN DAFP-1 AND TREHALOSE DIHYDRATE CRYSTALS

Figure 4A:
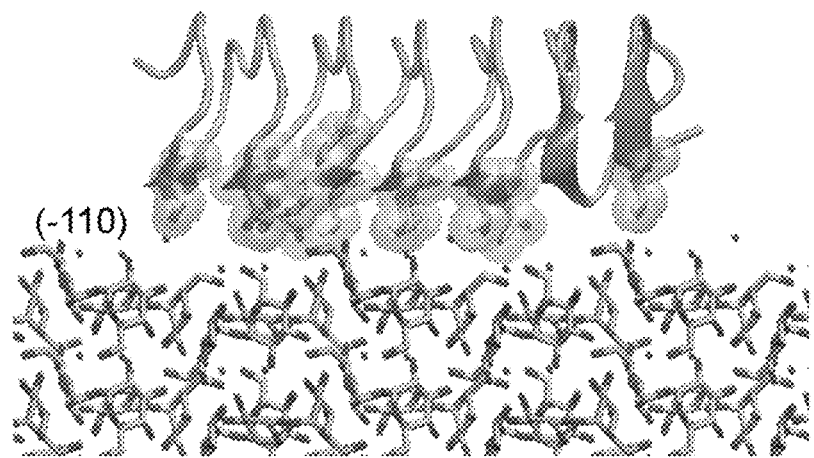
FIG. 4A shows a schematic representation of DAFP-1 recognizing the trehalose dihydrate crystal surface (−110).
Figure 4B:
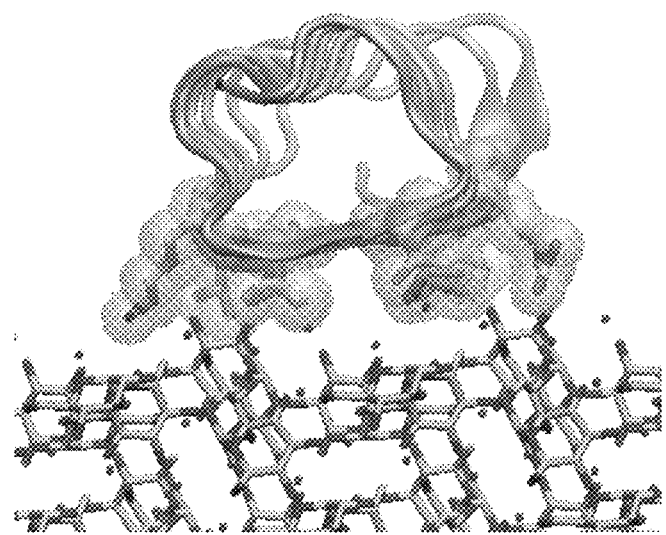
FIG. 4B shows a schematic representation related to FIG. 4A by a 90° rotation around the vertical axis.
Figure 4C:
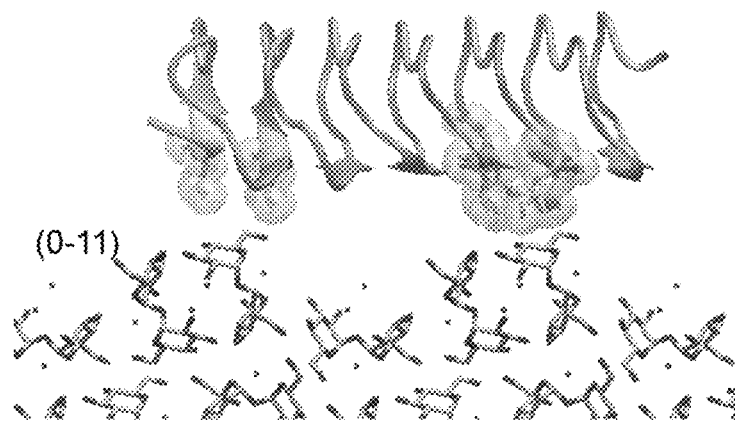
FIG. 4C shows a schematic representation of DAFP-1 recognizing the trehalose dihydrate crystal surface (0-11).
Figure 4D:
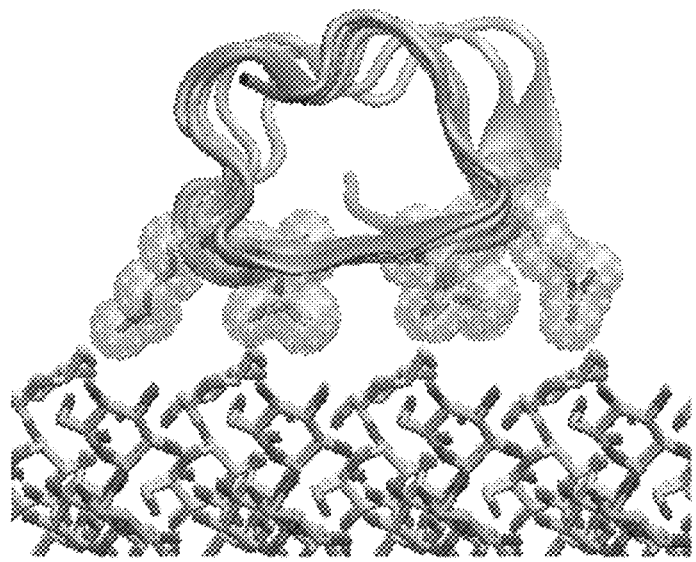
FIG. 4D shows a schematic representation related to FIG. 4C by a 90° rotation around the vertical axis.

To gain insights into the molecular recognition between DAFP-1 and trehalose dihydrate crystal surfaces, we performed molecular dynamics (MD) computational simulations to investigate the binding of DAFP-1 to two surfaces of trehalose dihydrate crystal. One trehalose dihydrate crystal surface is denoted as (−110) and a second trehalose dihydrate crystal surface is denoted as (0-11). The surface (−110) is a relatively fast-growing surface compared to surface (0-11) and the calculated surface energy ($E_{surf}$) of surface (−110) in the absence of the AFP is about 4% higher than that of surface (0-11). Upon the docking of the AFP, the calculated surface energies ($E'_{surf}$) of both surface (−110) and surface (0-11) significantly decrease, suggesting interactions between the AFP and the surfaces. The binding of the AFP to both surfaces ($\Delta\Delta E_{bind}$) is energetically favorable and results in the reduction of surface energies of both surfaces by about 40% (Table 3). FIGS. 4A and 4B show the AFP residue interaction with the trehalose dihydrate crystal surface (−110). FIGS. 4C and 4D show the AFP residue interaction with the trehalose dihydrate crystal surface (0-11).

In addition, FIGS. 4A and 4B and Table 4 show the hydrogen bonding interactions mainly between the conserved threonines on the putative flat ice-binding surface of the AFP and trehalose or water molecules on the trehalose dihydrate crystalline surfaces. In FIGS. 4A-4D, trehalose dihydrate is shown in licorice and the AFP is represented as a cartoon in pale purple and the residues forming hydrogen bonds with the sugar molecules on the crystal surface are represented as van der Waals spheres with licorice inside. There are about 40% fewer hydrogen bonds at the interface between the AFP and the surface (0-11) face than those between the AFP and the surface (−110) face (Table 4) due to the curvature of (0-11) surface (FIGS. 4A-4D). As shown in Table 4, there are eleven residues in the AFP involved in the binding to the (−110) trehalose dihydrate surface. Also as shown in Table 4, there are eight residues in the AFP involved in the binding to the (0-11) trehalose dihydrate surface.

As shown in FIGS. 4A-4D and Table 4, about 20% of the AFP residues form the relative flat ice-binding surface and about 10% of the AFP residues recognize the trehalose dihydrate crystalline surfaces. An antifreeze protein having about 10% conservation with any one of the proteins expressed in SEQ. ID 1, SEQ. ID 2, SEQ. ID 3 or SEQ. ID 4 would recognize the trehalose dihydrate crystalline surface and prevent the trehalose from crystallizing or precipitating in solution.

Molecular dynamics simulation methods. The starting 3D structure of DAFP-1 and the denatured DAFP-1 were created from a homology model of a *Tenebrio molitor* AFP, TmAFP (PDB code 1EZG). A fast-growing surface, (−110), and a relatively slow-growing surface, (0-11), of trehalose dihydrate crystal were investigated. The slabs of (−110) and (0-11) trehalose dihydrate crystal surfaces were constructed using Cerius² (Accelrys) from 4×4×4 and 8×3×3 supercells, respectively. The surface energies ($E_{surf}$) were computed as $E_{surf}=[E_{slab}-(N_{slab}/N_{bulk})E_{bulk}]/2A$ where, $E_{slab}$ is the potential energies of the surface slab and the bulk unit cell in vacuum at 0 K, respectively, $N_{slab}$ and $N_{bulk}$ are the number of molecules in the slab and the bulk unit cell, respectively, and A is the area of the surface unit cell. DAFP-1 and denatured DAFP-1 were manually docked on the (−110) and (0-11) surfaces of trehalose dihydrate by maximizing hydrogen bonding interactions between the protein and the molecules on the specific crystal surface of trehalose dihydrate, respectively.

TABLE 3

Surface energies for (−110) and (0-11) surfaces of trehalose dihydrate and the relative binding energies of DAFP-1 to these surfaces.

| Surface | $E_{surf}$ (mJ/m²) | System | $\Delta\Delta E_{bind}$ (kcal/mol) | $E'_{surf}$ (mJ/m²) |
|---|---|---|---|---|
| (−110) | 3086 | DAFP-1 + (−110) | −116 | 1825 |
| (0-11) | 2976 | DAFP-1 + (0-11) | −75 | 1692 |

TABLE 4

Possible Hydrogen Bonding Interactions between DAFP-1 and the Crystalline Surfaces of Trehalose Dihydrate, (−110) and (0-11).

| DAFP-1 + (−110) | | DAFP-1 + (0-11) | |
|---|---|---|---|
| DAFP-1 | (−110) | DAFP-1 | (0-11) |
| T3 O | TEL174 O14 | T3 O | TEL258 O38 |
| T26 O | TEL239 O40 | T16 O | TEL258 O40 |
| T29 O | WAT518 O | T51 O | TEL206 O38 |
| T39 O | TEL250 O28 | T53 O | TEL242 O38 |
| T41 O | WAT518 O | R54 Nη2 | TEL278 O40 |
| T51 O | TEL250 O16 | K62 Nζ | TEL170 O38 |
| T51 O | TEL250 O14 | T63 O | TEL206 O40 |
| R54 Nη2 | TEL170 O16 | T65 O | TEL242 O40 |
| R54 Nε | TEL170 O16 | | |
| K62 Nζ | WAT669 O | | |
| T63 O | TEL250 O16 | | |
| T65 O | WAT513 O | | |
| T77 O | WAT510 O | | |

A number of embodiments of the invention have been described. Nevertheless, it will be understood that various modifications may be made without departing from the spirit and scope of the invention. Accordingly, other embodiments are within the scope of the present invention.

We claim:

1. A method of inhibiting precipitation and/or crystallization of a sugar in a solution, comprising:
preparing the solution containing the sugar and an amount of at least one antifreeze protein effective to inhibit the precipitation and/or the crystallization of the sugar in the solution, wherein the sugar is selected from the group consisting of trehalose, glucose, fructose, lactose, sucrose and maltose, the antifreeze protein has a sequence of SEQ ID NO: 1, SEQ ID NO: 2, SEQ ID NO: 3, or SEQ ID NO: 4, the sugar has a first mass, the antifreeze protein has a second mass, and a ratio of the second mass to the first mass is from about 1:8000 to 1:260; and
storing the solution at a temperature of from $-20°$ C. to room temperature for at least two hours, wherein ice does not form in the solution during the storing.

2. The method of claim 1, wherein the solution contains water.

3. The method of claim 1, wherein the sugar is trehalose, lactose, sucrose or maltose.

4. The method of claim 3, wherein the sugar is trehalose.

5. The method of claim 1, wherein the antifreeze protein has the sequence of SEQ ID NO: 1.

6. The method of claim 5, wherein the solution further contains a second antifreeze protein, wherein the second antifreeze protein comprises one of the sequences of SEQ ID NO: 2, SEQ ID NO: 3, or SEQ ID NO: 4.

7. The method of claim 1, wherein the sugar is trehalose, the antifreeze protein has an antifreeze protein concentration, and the trehalose has a trehalose concentration, wherein the antifreeze protein concentration is from about 0.04 mg/mL to 1.0 mg/mL and the trehalose concentration is between about 30 mg/mL and about 400 mg/mL.

8. The method of claim 7, wherein the antifreeze protein and the trehalose are present in the solution in a molar ratio of the antifreeze protein to the trehalose of about $0.5 \times 10^{-5}$ to about $3 \times 10^{-2}$.

9. The method of claim 8, wherein the molar ratio of the antifreeze protein to the trehalose is about $2 \times 10^{-5}$ to about $7 \times 10^{-4}$.

10. The method of claim 1, further comprising lyophilizing the solution to prepare a powder, and reconstituting the powder.

11. The method of claim 1, wherein the temperature is from $-20°$ C. to $0°$ C.

12. The method of claim 1, wherein the solution is stored for a period of time of from a plurality of days to a plurality of months.

13. A method of protecting a biological sample in need of protection against sub-$0°$ C. temperatures, comprising:
preparing the solution according to the method of claim 1; and
administering an effective amount of the solution in vitro to the sample.

14. The method of claim 13, wherein the sample comprises a tissue, cells, a protein, a nucleic acid or an active pharmaceutical ingredient.

15. The method of claim 13, wherein the solution is prepared at room temperature.

16. The method of claim 13, wherein, after administering the solution to the sample, the sugar is present at a concentration from about 10 mg/mL to 680 mg/mL.

17. The method of claim 13, wherein, after administering the solution to the sample, the antifreeze protein is present at a concentration from 2 µg/mL to 10 mg/mL.

18. The method of claim 13, further comprising storing the sample at a sub-0 ° C. temperature.

19. A method of protecting a living organism in need of protection against sub-$0°$ C. temperatures, comprising:
preparing the solution according to the method of claim 1; and
administering an effective amount of the solution in vivo to the living organism.

20. The method of claim 19, wherein the solution contains water, and the sugar is trehalose.

* * * * *